US006896877B2

(12) United States Patent
Calello et al.

(10) Patent No.: US 6,896,877 B2
(45) Date of Patent: May 24, 2005

(54) COSMETIC COMPOSITIONS CONTAINING CROSSLINKABLE POLYMERS

(75) Inventors: Joseph Frank Calello, Union, NJ (US); Shichiu Kwan, Whitehouse Station, NJ (US); Alexander Lukacs, III, Wayne, PA (US); Anjali Abhimanyu Patil, Westfield, NJ (US); Barbara Ann Wolf, Scarsdale, NY (US); George Harvey Armstrong, New Kinsington, PA (US)

(73) Assignee: Revlon Consumer Products Corporation, New York, NY (US)

( * ) Notice: Subject to any disclaimer, the term of this patent is extended or adjusted under 35 U.S.C. 154(b) by 24 days.

(21) Appl. No.: 10/704,074

(22) Filed: Nov. 10, 2003

(65) Prior Publication Data

US 2004/0105876 A1 Jun. 3, 2004

Related U.S. Application Data

(63) Continuation of application No. 09/907,559, filed on May 10, 2001, now Pat. No. 6,680,049, which is a continuation of application No. 09/208,981, filed on Dec. 11, 1998, now Pat. No. 6,277,358.
(60) Provisional application No. 60/069,605, filed on Dec. 15, 1997.

(51) Int. Cl.$^7$ .................................................. A61K 7/06
(52) U.S. Cl. ..................... 424/70.1; 424/401; 424/70.6; 424/70.11; 424/70.19; 424/70.21
(58) Field of Search ................................ 424/401, 70.1, 424/70.6, 70.11, 70.19, 70.21, 70.22, 70.31

(56) References Cited

U.S. PATENT DOCUMENTS 6,680,049 B2 * 1/2004 Calello et al. ........... 424/78.02

* cited by examiner

Primary Examiner—Shelley A. Dodson
Assistant Examiner—Konata M. George
(74) Attorney, Agent, or Firm—Julie Blackburn

(57) ABSTRACT

A cosmetic composition which provides a semi-permanent, crosslinked film on a keratinous substrate comprising a film-forming polymer having functional groups capable of cross-linking upon exposure to a cross-linking agent reactive with the functional groups; a cross-linking agent reactive with the functional groups of the film-forming polymer; a dissipatable blocking agent which is operable prior to dissipation, to block the cross-linking agent from cross-linking the functional groups of the film-forming polymer, and which, after dissipation, leaves the cross-linking agent free to cross-link the functional groups of the film-forming polymer.

17 Claims, No Drawings

COSMETIC COMPOSITIONS CONTAINING CROSSLINKABLE POLYMERS

RELATED APPLICATIONS

This application is a continuation of U.S. Ser. No. 09/907,559, filed May 10, 2001, now U.S. Pat. No. 6,680,049 which is a continuation of U.S. Ser. No. 09/208,981, filed Dec. 11, 1998, now U.S. Pat. No. 6,277,358 which claims priority from Provisional Application Ser. No. 60/069,605, filed Dec. 15, 1997.

TECHNICAL FIELD

The invention is in the field of cosmetic compositions, in particular, crosslinkable, semi-permanent compositions for application to keratinous substrates such as nails, hair, or skin which contain crosslinkable film forming polymers; crosslinked, semi-permanent compositions on keratinous substrates such as nails, hair, or skin, which contain crosslinked film forming polymers; and processes for providing such semi-permanent, crosslinked compositions to the surface of keratinous substrates such as nails, hair, or skin, whereby crosslinking of the film forming polymer is effected after coating of the keratinous substrate.

BACKGROUND OF THE INVENTION

Film forming polymers are widely used in the cosmetic industry. The ability to form films on skin, lips, or hair is one of the main means of providing a cosmetic benefit. For example, materials such as film forming cationic polymers are found in hair conditioning agents. They are capable of depositing on the hair to form a film or coating which provides benefits varying from shine, to softness, manageability, and similar characteristics. Similarly, various film forming polymers may be found in color cosmetics such as lipsticks. These polymers may affect lipstick wear and adhesion, in addition to serving as a film to hold the pigments in place on the lips. Also, nail enamel compositions usually contain, as the main component, some type of film forming polymer. Such compositions are typically wholly liquid or comprise liquids which contain solid particulates in suspension. They are applied as liquids and, after drying, the film formed on the nail usually lasts for at least several days, although a key feature for such cosmetic applications is their removability. It is thus desirable to provide compositions which are semi-permanent, meaning that they demonstrate high durability on the coated substrate, but yet can be easily removed at will by the user using mechanical methods such as wiping or absorbing into a porous medium such as a tissue, as with lipsticks; or by chemical methods, for example, the removal of a nail enamel using an organic solvent such as ethyl acetate or acetone. In general, the types of polymeric materials used in cosmetics have a significant impact on providing, compositions with improved properties. Thus, cosmetics companies are always searching for new and different polymers to provide properties which improve cosmetic performance.

Cross-linkable, liquid compositions comprising polymers are known in the industrial coating industry. They are used in products such as paints, varnishes, lacquers, and the like, and are known to provide tough, resilient coatings which demonstrate good wear characteristics. These compositions usually contain a polymeric film former. They can also contain other desirable ingredients such as solvents, dispersants, coalescents, and the like, as well as some type of cross-linking agent or crosslinkable chemical moiety within the structure of the polymer. Some crosslinkable compositions of this type are two-part, two-pot systems, wherein one part contains the film forming polymer and the second part contains the crosslinking agent. Upon mixing, such compositions then immediately react to form the crosslinked coating. Other systems are two-part, one-pot systems, wherein the film forming polymer and the crosslinking agent are present in the same pot. Both two-part, two-pot systems and two-part, one-pot systems can each contain blocking agents; it is common practice to include a blocking agent in a two-part, one-pot system. The blocking agent blocks the cross-linking agent from reacting with the film-forming polymer to permit cross-linking while the composition is in the liquid form. Often the blocking agent is a volatile agent, so that after the coating is applied to the substrate and allowed to dry, the volatile blocking agent evaporates, and the cross-linking agent is then free to cross-link the reactive functional groups of the film forming polymer.

It is known to use cross-linkable monomeric coatings in the manufacture of artificial nail coatings, also known as "wraps" or "tips" to produce permanent coatings. For example, U.S. Pat. No. 4,104,333 teaches self-curing artificial fingernail compositions containing cross-linking monomers. The compositions are applied to the nail. The monomers polymerize, and then cross-link, forming a permanent, thick, artificial coating on top of the nail. If an elongated artificial nail is desired, an extender is affixed to the end of the nail. The monomer composition is applied over the nail and extender and allowed to harden. The extender is removed and the resulting artificial nail is shaped to the desired length. One disadvantage of these types of compositions is that they contain monomers, which are known to cause skin sensitivity in susceptible individuals. Another disadvantage is their permanence. The chemical nature of the polymerization of such compositions as well as the highly crosslinked nature of the polymerized coatings resulting from such coating compositions does not allow for easy removal of the film. In such instances where coating or repair of a nail surface is the desirable result of providing such polymerizable coatings, easy removability is a distinct advantage.

European Patent Application EP 752 244 teaches liquid coating compositions containing a polar organic solvent and comprising film forming acrylic polymers which are water soluble upon neutralization of polar organic groups contained within the film forming polymer, and which are deposited onto a nail surface from an aqueous medium. Upon evaporation of the liquids, a durable polymeric film is produced which demonstrates good adhesion to the nail surface. The compositions taught in EP 752 244 differ from the compositions of the invention because they do not contain a crosslinkable, film forming polymer. Furthermore, the coatings formed on the nail surface with the compositions taught in EP 752 244 are not crosslinked coatings.

One object of the invention is to provide cosmetic compositions comprising crosslinkable, film forming polymers.

Another object of the invention is to provide coated compositions containing crosslinked polymers, wherein the polymers are not obtained by polymerization directly on the skin, hair, or nail surface.

Another object of the invention is to provide semi-permanent cosmetic compositions containing crosslinked polymers which provide improved wear, adhesion, and other beneficial properties.

Another object of the invention is to provide a method for forming a film on a keratinous substrate which is more resistant to wear when compared with normal methods and preparations.

Another object of the invention is to provide liquid nail enamel compositions and liquid containing nail enamel compositions comprising crosslinkable, film forming polymers.

Another object of the invention is to provide a semi-permanent nail enamel composition containing crosslinked polymers, which provides good wear, adhesion, and gloss.

Another object of the invention is to provide semi-permanent nail enamel composition containing crosslinked polymers, which is made either without cellulose-based film formers, or containing significantly reduced levels of cellulose-based film formers.

Another object of the invention is to provide a method for forming a film on nails which is more resistant to wear when compared with normal methods and preparations.

Another object of the invention is to provide a water-based nail enamel composition containing crosslinkable polymers, which provides improved wear, adhesion, and gloss.

SUMMARY OF THE INVENTION

The invention is directed to a cosmetic composition which provides a semi-permanent, crosslinked film on a keratinous substrate, comprising:

(a) a film-forming polymer having functional groups capable of cross-linking upon exposure to a cross-linking agent reactive with said functional groups, (b) a cross-linking agent reactive with said functional groups of the film-forming polymer, (c) a dissipatable blocking agent which is operable (i) prior to dissipation, to block the cross-linking agent from cross-linking the functional groups of the film-forming polymer, and which, (ii) after dissipation, leaves the cross-linking agent free to cross-link the functional groups of the film-forming polymer.

In a preferred embodiment of the invention, the cosmetic composition comprises a one-pot composition comprising:

(a) a film-forming polymer having functional groups capable of cross-linking upon exposure to a cross-linking agent reactive with said functional groups, (b) a cross-linking agent reactive with said functional groups of the film-forming polymer, (c) a dissipatable blocking agent which is (i) operable prior to dissipation, to block the cross-linking agent from cross-linking the functional groups of the film-forming polymer, and which, (ii) after dissipation, leaves the cross-linking agent free to cross-link the functional groups of the film-forming polymer.

DETAILED DESCRIPTION

The cosmetic compositions of the invention are preferably for application to keratinous materials such as hair, skin, or nail, particularly nails and provide a semi-permanent cross-linked coating on such substrates. The components of the composition are as follows, with all percentages being percentages by weight of the total composition unless stated otherwise. The cosmetic compositions of the invention may also contain other desirable ingredients such as solvents, dispersants, coalescents, dyes and the like as well as solid, particulate components such as opacifiers and pigments. Particularly preferred compositions are solventless, i.e. free of aqueous or non-aqueous solvents.

The Film-Forming Polymer

The composition of the invention comprises a film-forming polymer which is characterized by having reactive functional groups which are capable of cross-linking upon exposure to a cross-linking agent which is reactive with the functional groups on the film-forming polymer. The term "film-forming" means that the polymer is capable of forming a film on keratinous material. By "film" is meant a continuous two-dimensional structure having a thickness of about 15 mils or less, preferably about 2 to 10 mils with "mil" referring to thousandths of an inch. Preferably, the film-forming polymer is present at 0.5–95%, more preferably 1–80%, most preferably 5–70% by weight of the total composition.

The film-forming polymer used in the compositions of the invention is already polymerized at the time it is applied to the skin, hair, or nails in the form of a composition. Only the cross-linking occurs after application of the cosmetic to the skin, hair, or nails. The film-forming polymer may be comprised of a variety of monomer units so long as the polymer contains enough reactive functional groups to permit cross-linking to a degree sufficient to provide a suitable, semi-permanent film on the keratinous material to which the cosmetic composition is applied. The film-forming polymer may be in the form of an oligomer, homopolymer, copolymer, terpolymer, graft or block copolymers as well as star and branched polymers. Suitable film-forming polymers in accordance with the invention can be made from monomers or oligomers which, after polymerization, have reactive functional groups such as hydroxyl; carboxyl; isocyanate; halogen; alkylene such as ethylene; carbonyl such as carbonyl compounds comprising reactive methylene groups such as acetoacetoxy, epoxy, amino, and the like. While the reactive functional groups mentioned above are, perhaps, those most commonly used to effect crosslinking, the above list is intended to be non-limiting and additional reactive functional groups are well known to those skilled in the art.

Examples of monomers which, after polymerization, will yield polymers having reactive, crosslinkable groups include monomers or oligomers which polymerize via a free radical, cationic, or anionic polymerization mechanism. For example acrylic acid, methacrylic acid, and the like polymerize by free radical mechanisms, and contain reactive carboxylic acid groups, including but not limited to those having monomer units of the formula:

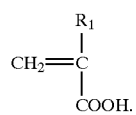

I wherein $R_1$ is H or a $C_{1-30}$ straight or branched chain alkyl, aryl, or aralkyl.

Examples of monomers capable of free radical polymerization which have reactive carboxylate groups include acrylates, and methacrylates, including but not limited to those having monomer units of the general formula:

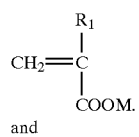

II and

-continued

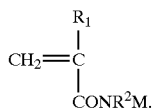

III wherein $R_1$ is as above defined, $R^2$ is H or a $C_{1-30}$ straight or branched chain alkyl, aryl, or aralkyl, and M is a $C_{1-30}$ straight or branched chain alkyl which is unsubstituted, or substituted with one or more substitutents which are hydroxyl, halogen, carboxyl, acetoacetoxy, or combinations thereof; pyrrolidone, or a substituted or unsubstituted aromatic, alicylic, or bicyclic ring where the substituents are $C_{1-30}$ straight or branched chain alkyl.

Examples of monomers capable of free radical polymerization which have reactive hydroxyl functional groups include hydroxyalkyl acrylates and hydroxyalkyl methacrylates, and other similarly hydroxy substituted organounsaturated monomers.

Examples of monomers or oligomers which, after polymerization, will yield polymers having reactive, crosslinkable groups also include monomers, macromonomers and oligomers which polymerize via a condensation polymerization mechanism involving two or more multifunctional monomers, macromonomers, or oligomers such as, for example, diacids, diesters, diamines, and diols. Thus, condensation polymers which are polyamides, polyesters, or polyimides which comprise reactive, crosslinkable groups as defined above are suitable film-forming polymers for the practice of this invention. Specific examples of multifunctional monomers, macromonomers, and oligomers and crosslinkable, film-forming polymers resulting from the condensation polymerization of such multifunctional monomers and oligomers are well known to those skilled in the art.

Examples of monomers, macromonomers and oligomers which, after polymerization, will yield polymers having reactive, crosslinkable groups also include monomers and oligomers which polymerize via an addition polymerization mechanism such as, for example, diisocyanates, epoxy resins, diamines, diols, and dialdehydes. Thus, addition polymers which are polyurethanes, polyimidazoles or cured epoxy resins which comprise reactive, crosslinkable groups as defined above are suitable film-forming polymers for the practice of this invention. Specific examples of multifunctional monomer, macromonomers and oligomers and crosslinkable, film-forming polymers resulting from the addition polymerization of such multifunctional monomers, macromonomers and oligomers are well known to those skilled in the art.

Suitable monomers, macromonomers, and oligomers may be wholly organic in nature, wholly inorganic in nature, or organic/inorganic hybrids. Correspondingly, the polymers resulting from the polymerization of such monomers, macromonomers and/or oligomers may be wholly organic in nature, wholly inorganic in nature, or an organic/inorganic hybrid. Examples of organic/inorganic hybrid polymers include, for example, the condensation polymers resulting from the polymerization of carbinol-terminated oligomeric dimethylsiloxanes with alkyl diisocyanates. Other examples of such organic/inorganic hybrid polymers include the compositions prepared by the two-step polymerization of monomers comprising acryloxy-substituted silicon atoms, the method of polymerization comprising an initial hydrolysis of the acryloxy-substituted silane to generate a silicate network, with subsequent free radical polymerization of the resulting acrylic acid derivatives to generate a polyacrylate/polysilicate interpenetrating network. Such "sol-gel" systems are well known to those skilled in the art.

Most often the film-forming polymer will contain more than one type of reactive functional group capable of cross-linking, i.e. a combination of carboxyl groups, isocyanate groups, hydroxyl groups, carbonyl groups and so on. Sometimes a single chemical moiety will contain two or more reactive functional groups. For example, an acetoacetyl group contains both a carbonyl group and an active methylene group, and can be incorporated into the chain of a wide variety of film-forming polymers, resulting in film-forming polymers having more than one reactive functional group that will participate in cross-linking.

Another moiety which contains more than one reactive functional group is an acetoacetamide group which contains a carbonyl group and an amide.

Alternatively, the composition may contain more than one film-forming polymer, each type having a different reactive functional group. For Example, European Patent Application 341 886/A2 teaches an aqueous coating composition which contain two types of vinyl polymers, one having chain pendant amine functional groups, and the second having chain pendant carbonyl-functional groups.

The Cross-Linking Agent

The term "cross-linking agent" means a chemical compound or reagent which is capable of reacting with the reactive functional groups of the film-forming polymer to cause cross-linking of the polymer. Such crosslinking agents can be monomeric, oligomeric, or polymeric in nature, and may comprise a plurality of identical or different chemical moieties which react with the reactive functional groups on the film forming polymer which is to be crosslinked. The term "crosslinked" means a polymer having chains or branches which have been joined together by a plurality of chemical cross-links.

Preferably, the compositions of the invention contain 0.1–70%, more preferably 0.5–60%, most preferably 1–55% by weight of the total composition of crosslinking agent. A wide variety of crosslinking agents may be used, so long as they are reactive with the free functional groups of the film forming polymers and, after reaction with these functional groups, provide a crosslinked composition which provides a semi-permanent film on the keratinous substrate being coated. By "semi-permanent" is meant that the film provides acceptable durability to the wearer during the course of normal wear as is customary for the cosmetic application of interest, but can be selectively removed by the wearer at will by mechanical or chemical means.

The type of crosslinking agent used will depend on the nature of the reactive groups in the film-forming polymer being used, since certain crosslinking agents are specific to certain crosslinkable functional groups.

For example, various metal ions having a coordination number of greater than or equal to 2 and less than or equal to 6 are suitable cross-linking agents for film-forming polymers having free carboxylate groups. Examples of such metals include calcium, magnesium, zinc, titanium, zirconium, and the like. Preferred metal ions are metal ions which have coordination numbers of 2 to 4.

Multifunctional alcohols are suitable cross-linking agents for film-forming polymers having free isocyanate or epoxy groups, such as multifunctional polyisocyanates or multifunctional epoxy resins. Examples of suitable alcohols include aliphatic or aromatic dihydric alcohols or polyols. Preferred are aliphatic dihydric alcohols having 1–10 carbon atoms, such as propylene glycol, butylene glycol, and so on, or non-polymeric polyols having 1–10 carbon atoms, containing three or more hydroxyl groups per molecule, such as glycerine, ascorbic acid, glucuronic acid, glucose, lactose, xylitol, lactose, mannitol, and so on. Polymeric polyols are also suitable cross-linking agents, including polyvinylalcohol; or homopolymeric or block copolymeric ethers formed by the polymerization of monomeric alkylene oxides. Examples of such ethers include polyethylene glycol, ethylene glycol/propylene glycol copolymers, block copolymers of oxyethylene and oxypropylene, and the like.

Various multifunctional primary, secondary, and tertiary amines are suitable as cross-linking agents for film-forming polymers having epoxy groups, such as multifunctional polymeric epoxy resins. Such amines exhibit the general formulas $RNH_2$, RR'NH or RR'R"N respectively, wherein R, R', and R" are each independently a multivalent aliphatic, aromatic, or heterocyclic moiety, such as a $C_{1-25}$ straight or branched chain alkyl; aryl, or a heterocyclic ring, all of which can be substituted with additional crosslinking substituents such as amino, halogen, hydroxyl, and the like.

Also suitable as cross-linking agents for film-forming polymers containing hydroxyl groups, such as polyalcohols, are classes of compounds such aldehydes, thermosetting resins, and salts of multi-valent anions. Suitable aldehydes have the general formula RCHO where R is hydrogen, or an aliphatic, alicylic, aromatic, or heterocyclic moiety. Preferred are aliphatic or aromatic aldehydes such as acetaldehyde, benzaldehyde, cinnamal, citral, dibutylene tetrafurfural, formaldehyde, furfural, glutaral, glyoxal, glutaraldehyde, hydroxyadipaldehyde and mixtures thereof.

While beyond the practical scope of this disclosure, it will be appreciated by one of average skill in the art that a wide variety of crosslinking agents are suitable for the practice of this invention, the choice of which is highly dependent on the nature of the crosslinkable, film-forming polymer of interest.

The cross-linking agent may be a separate ingredient added to the compositions of the invention, or it may form a part of the film-forming polymer itself. Examples of where the cross-linking agent is a component of the film-forming polymer itself, include amine-functional polyacrylates or methacrylates, further comprising acetoacetoxyethyl groups. In such compositions a suitable blocking agent must be present to inhibit crosslinking before application. Such suitable crosslinking agents are described below.

The Blocking Agent

The blocking agent can be monomeric, oligomeric, or polymeric, and can be present in the cross-linkable composition in a variety of forms. The blocking agent can be inherent to the composition of the film-forming polymer or polymers used or the crosslinking agent as, for example, an appended chemical moiety to the polymer chain, or can be a separate ingredient such as, for example, an additive or a solvent which is used in the cosmetic formulation. The blocking agent must be dissipatable, which means that prior to use of the composition containing it, the blocking agent blocks the cross-linking reaction. However, after the composition is applied to the keratinous substrate, the blocking agent is rendered ineffective in blocking the cross-linking reaction, either by disappearing, for example through evaporation, or changing form so that it becomes chemically inactive through chemical reaction or other mechanisms. An essential feature of the blocking agent is that it inhibits, or prevents, cross-linking of the cross-linkable coating composition until application on the keratinous substrate. The compositions of the invention contain 0.001–40%, preferably 0.01–30%, more preferably 0.5–20% by weight of the total composition of the blocking agent.

The following non-limiting examples of suitable blocking agents are provided to demonstrate the wide variety of forms which the blocking agent can assume. The exact nature and composition of the blocking agent is, of course, composition specific. Inhibitors for any specified coating composition can thus be many and varied and depend on the exact nature of the chemical cross-link which is being effected in the coating composition and can be readily ascertained by an individual skilled in the art.

For instance, a coating composition containing a film forming polymer comprising acetoacetoxy groups and a cross-linking agent comprising a multifunctional amine selectively cross-links by formation of covalent, enamine bonds and concurrent formation of water by-product. Such a cross-linking mechanism has been found to be inhibited, for instance, by the addition of volatile, monomeric acetoacetyl compounds such as those taught in WO 94/21738 assigned to Zeneca, Limited, which evaporate upon application of the coating composition to a substrate.

This same composition can be inhibited from cross-linking by providing to the composition a volatile base, such as a tertiary amine. In such instances the composition is stable to cross-linking providing a high pH is maintained. Upon application of the coating composition to the keratinous substrate, the added volatile base then evaporates, the pH of the composition decreases, and enamine cross-linking is facilitated.

Such film forming polymers comprising acetoacetoxy groups can also be crosslinked using ethylenically unsaturated cross-linking agents by means of a Michael reaction. In such instances, the active methylene groups of the acetoacetoxy moiety will react at ambient temperature with an electron deficient, multifunctional olefin, such as trimethylolpropane triacrylate under basic conditions. In such cases, cross-linking can be blocked by providing to such compositions an acidic ingredient which maintains a low pH until it is desired to effect cross-linking. Such an acidic ingredient can volatilize during use, or could be induced to decompose by, for example, providing an energy input such as heat or light, thereby enabling the cross-linking mechanism to occur.

An additional cross-linking mechanism which can be utilized when film forming polymers comprising acetoacetoxy groups are used in the cross-linkable cosmetic composition of this invention, involves acetoacetyl group tautomerism. The acetoacetyl group exists not only in the keto form, but in equilibrium with the enol form. The acetoacetoxy group exists in both forms under normal conditions in a 75:25 keto-to-enol ratio. Metal ions can chelate between the ester carbonyl and the enolic hydroxy of the enol form of the acetoxy group. When such metal ions have coordination numbers of greater than or equal to 2 and less than or equal to 6, such as zinc or zirconium, metal cross-links can be formed between polymer chains. Inhibiting agents for such compositions can comprise loosely coordinated organic ligands which coordinate to the metal ions but which, upon application of the cosmetic composition to the keratinous substrate, become labile as the cosmetic carrier phase volatilizes. The effect is entropic, with the favored crosslinked coating composition comprising acetoacetoxy chelated metal ions as cross-links between polymer chains.

Another type of cross-linking mechanism that can be used is set forth in PCT WO 97/23516, which is hereby incorporated by reference. This particular mechanism requires a polymer system capable of cross-linking by a process which includes reaction of a cyclic carbonate group with an amine group. In this case, the polymer contains cyclic carbonate functional groups and/or amine or amine precursor functional groups. Then a coating is formed with the composition, the polymer becomes cross-linked during and/or after film formation, primarily through the reaction of the cyclic carbonate groups with the amine groups.

A preferred embodiment of the instant invention utilizes a cosmetically acceptable carrier phase as the cross-linking inhibitor. In such instances the cosmetically acceptable carrier phase is often a solvent. When a solvent is used as the blocking agent in a cosmetic formulation, it can be either an aqueous or a non-aqueous solvent. In many such cases the crosslinking of the film-forming polymer, either as a single ingredient which additionally comprises the crosslinking agent or as a component of a composition which additionally comprises a separate crosslinking agent, is concentration dependent. This is the case with certain, crosslinkable compositions comprising, for example, azetidinium groups (which self-crosslink through the azetidinium groups) or film-forming polymer compositions comprising a film-forming polymer having appended acetoacetoxy groups and further comprising a multifunctional amine In these instances the solvent is used to maintain a suitably low concentration of the crosslinkable, film-forming polymer and, if applicable, an added crosslinking agent in a one-pot, cosmetic composition until application to a keratinous substrate. Once applied to the keratinous substrate, the process of solvent evaporation serves to raise the concentration of the crosslinkable, film-forming polymer and, if applicable, the added crosslinking agent in the applied film, thereby promoting the crosslinking of the film-forming polymer. While such solvents can be aqueous or non-aqueous, aqueous solvents are more preferred. Such aqueous solvents can consist entirely of water or can additionally comprise organic solvents. A solvent which consists entirely of water is most preferred.

The Cross-Linking Mechanism

The bonds which form between the cross-linking agent and the reactive functional groups of the film forming polymer may be hydrogen bonds, ionic bonds, dative bonds, covalent bonds, or mixtures of thereof. While each of these bond types are suitable for the practice of crosslinking film-forming polymers according to the invention, it is preferred that high strength crosslinks between polymer chains are established. Thus, compositions comprising hydrogen bonded crosslinks are least preferred. More preferred are compositions comprising datively or ionically bonded crosslinks. Most preferred are compositions comprising covalently bonded crosslinks.

Cross-linking which occurs via the formation of hydrogen bonds is illustrated in a wide variety of film-forming polymers, including but not limited to urethanes, acrylics, acrylonitriles, and so on. Hydrogen bonds are generally weaker than dative, ionic, or covalent bonds, and relatively higher concentrations of reactive functional groups are required. Cross-linking which occurs via the formation of hydrogen bonds may be illustrated in polyurethanes, where the cross-linking occurs between the NH groups and carbonyl groups of the polymer. In another example, in acrylonitrile polymers, the free cyano groups will hydrogen bond with the carboxyl groups.

The cross-linking may also occur by metal complexation of the reactive functional groups of the film-forming polymer. In such compositions the nature of the bond may be either dative, ionic, or covalent. Suitable metal cross-linking agents are as mentioned above. An example of cross-linking which occurs via the formation of metal complexes is seen with the film-forming polymer polyacrylic acid, which is crosslinked with zinc compounds such as zinc oxide.

The bonds which form between the reactive functional groups of the film-forming polymer and the cross-linking agent may be entirely covalent. Covalent bonds are generally the strongest and are often not reversible. Examples of cross-linking reactions which occur via the formation of covalent bonds are ether bonded cross-links, enamine bonded crosslinks, and ester bonded crosslinks.

Coating Methods

The compositions of the invention may be applied to the keratinous substrate using a variety of methods commonly practiced for application of cosmetic products. For example, if the compositions are applied to nails, suitable containers include bottles with brush applicators, nail enamel pens, and similar items. If the compositions of the invention are applied to artificial nails, they can be sprayed on, or the nails can be dipped in the composition.

If the compositions of the invention are applied to skin, such as with lipsticks, traditional lipstick dispensers, pots, and the like are suitable.

If the compositions of the invention are applied to facial skin, or eyelids, cheeks, and the like, containers such as compacts, pots, and jars may be used.

As previously mentioned, the compositions may contain solvent, or they may be solventless. If the latter, they do not contain any aqueous or non-aqueous solvents.

A wide variety of crosslinked cosmetic compositions may be made using the cross-linkable compositions of this invention, including but not limited to nail enamels, lotions, creams, makeup, lipstick, blush, eyeshadow, shampoo, conditioner, and other hair care and skin care products, including but not limited to those set forth below.

Nail Enamels

Suitable nail enamel compositions may be water-based, solvent-based, or solventless, and contain about 1–80% of the cross-linkable film forming polymer, 0.1–70% of the cross-linking agent, and 0.001–40% blocking agent. If a solvent is present, the solvent may be aqueous or non-aqueous or a mixture of both types of solvents. Suitable non-aqueous solvents include aliphatic or aromatic ketones such as acetone, diacetone alcohol, dihydroxyacetone, ethyl butyl valerolactone, methyl ethyl ketone, and the like; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate, hexyl alcohol, isopropanol, and the like; glycol ethers; esters such as butyl acetate, ethyl. acetate, etc.

The nail enamel compositions may be pigmented or clear. If pigmented, generally 0.1–30% by weight of the total composition, preferably 0.5–20%, more preferably 1–15% of pigment is suggested. Pigments suitable for use in nail enamel compositions are well known and include iron oxides, D&C and FD&C colors, titanium dioxide, and the like. The pigments may be treated or coated with agents which modify the surface properties such as silicones or acrylates. Examples of silicone treated pigments which can be used in the compositions of the invention are set forth in U.S. Pat. No. 4,832,944, which is hereby incorporated by reference.

If the nail enamel compositions of the invention contain pigments, it is desireable to also incorporate 0.1–15% by weight of the total composition of a suspending agent which acts to suspend the pigments in the formulation. Suitable suspending agents are montmorillonite minerals and derivatives thereof, such as stearalkonium bentonite, hectorites, attapulgite, bentones, and the like, as well as polymeric compounds known as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl.

It may be desireable to add small levels of other film formers such as cellulosic film formers. Suitable cellulosic film formers include nitrocellulose, cellulose acetate isobutyrate, cellulose acetate propionate, and the like. If cellulosic film formers are added, a level of 0.1–15%, preferably 0.5–7%, more preferably 0.5–5% by weight of the total composition is suggested.

The nail enamel compositions are applied to the nail by a variety of techniques, such as brushing, spraying or dipping. After the nail surface is coated, the blocking agent dissipates, leaving the cross-linking agent free to cross-link the reactive functional groups on the cross-linkable film-forming polymer.

Lipstick

Suitable lipstick compositions may contain, in addition to the ranges of cross-linkable polymer, cross-linking agent and blocking agent mentioned above, about 0–70% wax, 0–60% oil, and 0–50% particulate matter.

If the lipstick compositions contain oil, 10–50%, more preferably 10–40% oil can be used. The oils used may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C.

If the cosmetic compositions of the invention are transfer resistant sticks, significant amounts of volatile liquid solvent will most likely be present. Typically, such volatile solvent substitutes for a significant fraction of a non-volatile oil component in these lipstick compositions. The practical consequence of this substitution is twofold: (1) It enables the fabrication of a soft, compliant stick product which can easily deposit a continuous film on the lip when applied, and (2) It provides for a high effective solids content of the lipstick product on the lip after volatile solvent evaporation. In such high solids content lip films, color transfer is minimal since very little non-volatile oil component is present to carry pigment away from the lip.

In such transfer resistant lipsticks the volatile solvent can also act as a crosslink blocking agent in the practice of the current invention. Many lipsticks may comprise polymers which contain polar groups, such as waxes having a high acid number. In such compositions the carboxylic acid groups may be capable of crosslinking through hydrogen bonding. By solvating such crosslinkable polymers, hydrogen bonding can be disrupted until solvent evaporation occurs, thus blocking polymer crosslinking. Once solvent evaporation occurs, hydrogen bonding can then ensue and a highly durable lip film results. Preferred in such compositions are crosslinkable polymers or waxes which comprise a high fraction of polar groups capable of hydrogen bonding.

Suitable volatile solvents generally have a viscosity of 0.5 to 10 centistokes at 25° C. Suitable volatile oils include linear silicones, cyclic silicones, paraffinic hydrocarbons, or mixtures thereof.

Cyclic silicones (or cyclomethicones) most commonly used are of the general formula:

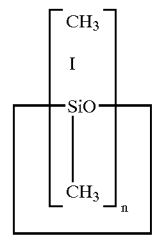

where and n=3–7.

Linear volatile silicones most commonly used in accordance with the invention have the general formula:

where n=0–7, preferably 0–5.

While the above described volatile silicones comprise organic groups which are exclusively methyl, it is well understood by one skilled in the art that such volatile silicones may also comprise repeat units which contain silicon-bonded groups, such as hydrogen or higher carbon-content alkyl radicals.

Examples of linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic ydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the cosmetic compositions of the invention. Suitable nonvolatile oils generally have a viscosity of greater than 10 centipoise at 25° C., and may range in viscosity up to 1,000,000 centipoise at 25° C. Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference.

Suitable oils may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as oils are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as oils are nonvolatile hydrocarbons such as isoparaffins, hydrogenated polyisobutene, mineral oil, squalene, petrolatum, and so on.

Straight or branched chain fatty alcohols having the formula R—OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as oils are various lanolin derivatives such as acetylated lanolin, acetylated lanolin alcohol, and so on.

Nonvolatile silicones, both water soluble and water insoluble, are also suitable as an oil component. Such silicones preferably have a viscosity of 10 to 600,000 centistokes, preferably 20 to 100,000 centistokes at 25° C. Suitable water insoluble silicones include amodimethicone, bisphenylhexamethicone, dimethicone, hexadecyl methicone, methicone, phenyl trimethicone, simethicone, dimethylhydrogensiloxane, stearoxytrimethylsilane, vinyldimethicone, and mixtures thereof Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Also suitable as oils are nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

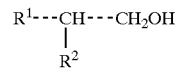

with a carboxylic acid having the general formula:

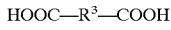

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Preferably, the guerbet ester is a fluoro-guerbet ester which is formed-by the reaction of a guerbet alcohol and carboxylic acid (as defined above), and a fluoroalcohol having the following general formula:

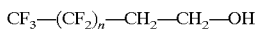

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Ga. as Developmental Ester L61125A, under the tradename Silube GME-F. Preferably, the lipsticks of the invention contain a mixture of volatile and nonvolatile oils, so that the amount of volatile oil is about 0–50%, preferably 5–40%, more preferably 10–30% by weight of the total composition, and the amount of nonvolatile oil is about 1–50%, preferably 5–40%, more preferably 10–30% by weight of the total composition.

The lipstick compositions may also contain 0–50%, preferably 7–45%, more preferably 10–40%, by weight of the total composition, of particulate matter having a particle size of 0.02 to 100, preferably 0.5 to 100, microns. The particulate matter may be colored or non-colored (for example white). Suitable particulates include bismuth oxychloride, titanated mica, fumed silica, spherical silica, polymethylmethacrylate, polyethylene, polypropylene, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature. The particulates may also include various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof. Preferably the composition will contain both pigmented and non-pigmented particulates. Obviously the percentage of pigments used in the particulate phase will depend on the type of cosmetic being formulated. Color cosmetics generally have a much higher concentration of color than other types of cosmetics. Generally the weight ratio of pigmented to non-pigmented particulates range from 1:50 to 50:1. It should be noted that particulates that are white or have no color are considered non-pigmented particulates in accordance with the invention, while particulates which exhibit color other than white are considered pigmented particulates in accordance with the invention.

The lipstick composition may also contain 0–70%, preferably 1–30%, more preferably 1–25% by weight of a cosmetically acceptable natural or synthetic wax. The waxes that can be used are solid or semi-solid waxes having a melting point of 30 to 120° C. and generally includes animal waxes, plant waxes, mineral waxes, silicone waxes, synthetic waxes, and petroleum waxes.

Examples of waxes in accordance with the invention include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, PEG-6 beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, stearoxy dimethicone, dimethicone behenate, stearyl dimethicone, and the like, as well synthetic homo- and copolymer waxes from the ethylene series. In the preferred embodiment of the invention the waxes are polymers of ethylene and/or propylene.

When a wax is used, the composition of the invention preferably contains fluorinated waxes, either alone or in addition to the above-mentioned natural or synthetic waxes, such as the fluorinated dimethicone copolyols disclosed in U.S. Pat. No. 5,446,114, which is hereby incorporated by reference, having the general formula:

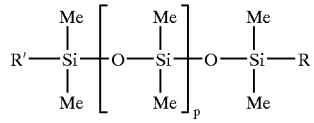

wherein:
p is an integer ranging from 1 to 2,000;
Me is methyl;
R' is —(CH$_2$)$_3$—O—(EO)$_a$—(PO)$_b$—(EO)$_c$—H;
R is —(CH)$_2$)$_2$—(CF$_2$)$_s$—CF$_3$;
R is an integer ranging from 1 to 13;
a, b, and c are each independently integers ranging from 0 to 20;
EO is —(CH$_2$CH$_2$—O)—; and
PO is —(CH$_2$CH(CH$_3$)—O)—.

Particularly prefered is a compound, dimethiconol fluoroalcohol dilinoleic acid, which is sold by Siltech, Inc., under the tradename Silwax F.

It may be desireable to include other ingredients in the lipstick formulation, in particular certain ingredients which enhance shine of the finish provided by the cosmetic composition of the invention. About 5–60%, preferably 5–50%, more preferably 7–45% of shine enhancers are suggested. Examples of shine enhancing ingredients are homo- or copolymers which are clear, or in other words have an index of refraction of 1.5 or greater. Examples of clear polymers are alkylated polyvinylpyrrolidones sold by International Specialty Products under the GANEX tradename. These polymers are copolymers of vinylpyrrolidone and long chain alpha olefins; and have the following general formula:

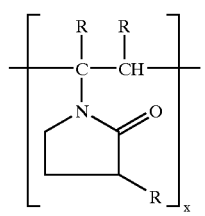

wherein R is H or a C$_{1-40}$ straight or branched chain alkyl, preferably a C$_{6-22}$ straight or branched chain alkyl. Examples of such polymers are disclosed in U.S. Pat. Nos. 4,514,271, 3,423,381, 3,423,381, and 3,417,054, all of which are hereby incorporated by reference. The composition preferably comprises 0.5–35%, preferably 1–20%, more preferably 1–15% of a C$_{6-22}$ alkylated polyvinylpyrrolidone. Particularly preferred are PVP/eicosene copolymer and PVP/hexadecene copolymer, and in particular PVP/eicosene copolymer.

Also suitable are polyvinylpyrrolidone (PVP) homopolymers, which may be purchased from International Special Products under the PVP-K tradename, in particular PVP K-15, PVP K-30, PVP K-60, PVP K-90, PVP K-120.

PVP/acetate copolymers, which are copolymers of vinylpyrrolidone and vinylacetate, are also suitable shine enhancers. Such polymers are sold under the PVPJVA tradename by International Specialty Products.

Also suitable shine enhancers are monoalkyl esters of poly(methylvinyl ether/maleic acid), which are sold by International Specialty Products under the GANTREZ tradename.

It may also be desired to add other ingredients such as preservatives, antioxidants, vitamins, emulsifiers, and the like.

When the lipstick compositions of the invention are applied to the lips, as they dry, the blocking agent dissipates, causing the film-forming polymer to cross-link on the lips to provide a semi-permanent film.

Hair Conditioners

In addition to the ranges of cross-linkable polymer, cross-linking agent, and blocking agent mentioned above, hair conditioning agents in accordance with the invention generally comprise 0.1–20% cationic conditioning agent, 0.1–30% fatty alcohol, 0.001–10% nonionic surfactant, and 5–95% water. Suitable cationic conditioning agents are cationic polymers, quaternary ammonium salts or the salts of fatty amines. Quaternary ammonium salts have the formula:

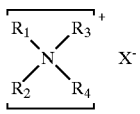

wherein $R_1$ is an aliphatic group of 1 to 22 carbon atoms, or aromatic, aryl, or alkaryl group having 12 to 22 carbon atoms; $R_2$ and $R_3$ are each independently an aliphatic group having 1–22 carbon atoms; and $R_4$ is an alkyl group of from 1 to 3 carbon atoms, and X is an anion selected from halogen, acetate, phosphate, nitrate and methyl sulfate radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, Other quaternary ammonium salts useful as the cationic conditioning agent are compounds of the general formula:

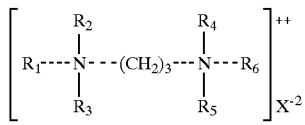

wherein $R_1$ is an aliphatic group having 16 to 22 carbon atoms, $R_2$, $R_3$, $R_4$, $R_5$, and $R_6$ are the same or different and are selected from alkyls having 1 to 4 carbon atoms and X is an anion as above defined.

Amides which exhibit the general formulas set forth below are also suitable conditioning agents:

wherein R is a straight or branched chain saturated or unsaturated alkyl having 6 to 30 carbon atoms, n is an integer from 1 to 4, and X and Y are each independently H, or $C_{1-6}$ lower alkyl. Preferred is an amide of the formula:

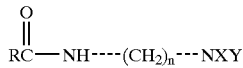

wherein R is a $C_{12-22}$ straight or branched chain alkyl, n is an integer from 1 to 4, and X is lower alkyl, preferably methyl.

Also suitable are amidoamine salts, which are the condensation products of fatty acids with a polyfunctional amines, for example, those having the formula $RCONH(CH_2)_nNR_1R_2$ where RCO is a fatty acyl group such as stearoyl, $R_1$ and $R_2$ are methyl or ethyl, and n is 2 or 3. Examples of such compounds include stearmidopropyl dimethylamine. Particularly preferred are amidoamine compounds complexed with a mild dimer acid, such as di(behenamidopropyl dimethyl amine) dimer dilinoleate or di(linoleamidopropyl dimethyl amine) dimer linoleate. Both ingredients are sold by Alzo, Inc. under the NECON tradename.

Also, quaternary imidazolinium salts having the following general formula are suitable as the cationic conditioning agent:

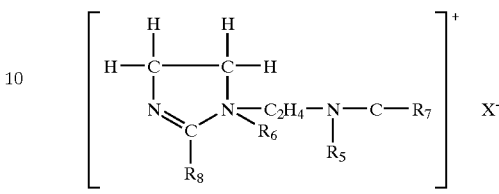

wherein $R_5$ is hydrogen or a $C_{1-4}$ alkyl; $R_6$ is a $C_{1-4}$ alkyl; $R_7$ is a $C_{8-22}$ alkyl; and $R_8$ is or a $C_{1-22}$ alkyl; and X is an anion as defined above.

Also suitable as the cationic hair conditioning agent are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic conditioning agent are cationic polymers such as:

(a) quaternary derivatives of cellulose ethers such as polymers sold under the tradename JR-125, JR-400, JR-30M.

(b) copolymers of vinylpyrrolidone having monomer units of the formula:

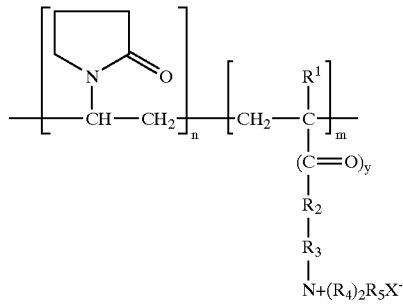

wherein $R_1$ is hydrogen or methyl, preferably methyl;
y is 0 or 1, preferably 1
$R^2$ is 0 or NH, preferably NH;
$R^3$ is $C_xH_{2x}$ where x is 2 to 18, or $-CH_2-CHOH-CH_2-$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(c) Homopolymer of dimethyldiallylammonium chloride, or copolymer of dimethyldiallylammonium chloride and acrylamide. Such compounds are sold under the tradename MERQUAT by Merck.

(d) Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters.

(e) cationic silicones. As used herein, the term "cationic silicones" means any silicone polymer or oligomer having a silicon backbone, including polysiloxanes, having a positive charge on the silicone structure itself. Cationic silicones that may be used in the compositions of the invention include those corresponding to the following formula:

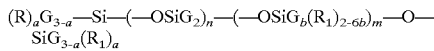

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the n+m is a number from 1 to 2,000 and is preferably 50 to 150; n is a number from 0 to 2000, and is preferably 50 to 150; and m is an integer from 1 to 2000, and is preferably 1 to 10; and $R_1$ is a monovalent radical of the formula $C_qH_{2q}L$ in which q is an integer from 2 to 8 and L is selected from the groups:

—N($R_2$)$CH_2$—$CH_2$—N($R_2$)$_2$

—N($R_2$)$_2$

—$\overset{+}{N}$($R_2$)$_3$A$^-$

—$\overset{+}{N}$($R_2$)$CH_2$—$CH_2$—$\overset{+}{N}R_3H_2$A$^-$ in which $R_2$ is selected from the group consisting of H, phenyl, benzyl, a saturated hydrocarbon radical, and is preferably an alkyl radical containing 1–20 carbon atoms; and A— is a halide ion.

(f) polymeric quaternary ammonium salts such as Polyquaternium 31, 33, 34, 35, 36, 37, and 39.

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

The preferred compositions of the invention contain 0.5–15% by weight of a cationic conditioning agent which is selected from the group:

(a) quaternary ammonium salts have the formula:

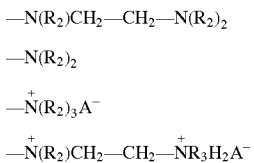

wherein $R_1$ is an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals;

(b) cationic silicones having the following formula:

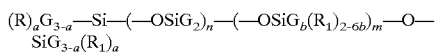

wherein G is H, phenyl, OH, $C_{1-10}$ alkyl; a is 0 or an integer from 1 to 3; b is 0 or 1; the sum n+m is a number from 1 to 2,000; n is a number from 0 to 2000; and m is an integer from 1 to 2000; and $R_1$ is a monovalent radical of the formula $C_qH_{2q}L$ in which q is an integer from 2 to 8 and L is selected from the groups:

—N($R_2$)$CH_2$—$CH_2$—N($R_2$)$_2$

—N($R_2$)$_2$

—$\overset{+}{N}$($R_2$)$_3$A$^-$

—$\overset{+}{N}$($R_2$)$CH_2$—$CH_2$—$\overset{+}{N}R_3H_2$A$^-$ in which $R_2$ is H, phenyl, benzyl, a saturated hydrocarbon radical, and is preferably an alkyl radical containing 1–20 carbon atoms; and A— is a halide ion; and (c) an-amide of the formula:

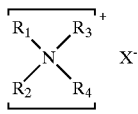

wherein R is a $C_{12-22}$ straight or branched chain alkyl, n is an integer from 1 to 4, and X is lower alkyl, preferably methyl, (d) an amidoamine salt, and mild dimer acids thereof Particularly preferred is where the cationic conditioning agent is selected from trimethylsilylamodimethicone, cetrimonium chloride, behentrimonium chloride, di(behenamidopropyl dimethyl amine) dimer dilinoleate, di(linoleamidopropyl dimethyl amine) dimer linoleate, or mixtures thereof.

Hair conditioning compositions may contain, preferably 0.5–10%, more preferably 1–8% of a fatty alcohol having the formula $RCH_2OH$ wherein R is a straight or branched chain saturated or unsaturated alkyl having at least about 6 to 30 carbon atoms. Examples of fatty alcohols suitable for use include behenyl alcohol, $C_{9-15}$ alcohols, caprylic alcohol, cetearyl alcohol, cetyl alcohol, coconut alcohol, decyl alcohol, lauryl alcohol, cetyl alcohol, myristyl alcohol, oleyl alcohol, palm alcohol, stearyl alcohol, tallow alcohol, and the like. The preferred compositions of the invention include a mixture of cetyl and stearyl alcohols.

Hair conditioning compositions also generally contain about 0.001–10%, preferably 0.01–8%, more preferably 0.01–5% of a nonionic surfactant or emulsifier.

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol with ethylene oxide, and the number of repeating ethylene oxide units in the molecule is 20.

Also suitable as the nonionic surfactant are alkoxylated carboxylic acids, which are formed by the reaction of a carboxylic acid with an alkylene oxide or with a polymeric ether. The resulting products have the general formula:

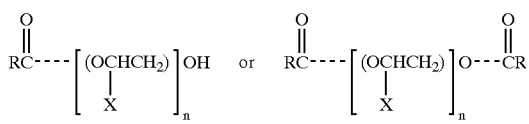

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

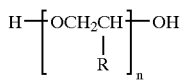

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w / M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature-due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane surfactant used in the invention may have any of the following general formulas:

$M_xQ_y$, or $M_xT_y$, or $MD_xD'_yD''_zM$ wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D'', x, y, and z are as set forth below, with the proviso that the compound contains at least one hydrophilic radical and at least one lipophilic radical.

Preferred is a linear silicone of the formula:

$MD_xD'_yD''_zM$ wherein $M = RRRSiO_{1/2}$

D and $D' = RR'SiO_{2/2}$ $D'' = RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M=trimethylsiloxy $D = Si[(CH_3)][(CH_2)_nCH_3]O_{2/2}$ where n=0–40, $D' = Si[(CH_3)][(CH_2)_o-O-PE]O_{2/2}$ where PE is $(-C_2H_4O)_a(-C_3H_6O)_bH$, o=0–40, a=1–100 and b=1–100, and $D'' = Si(CH_3)_2O_{2/2}$ More specifically, suitable silicone surfactants have the formula:

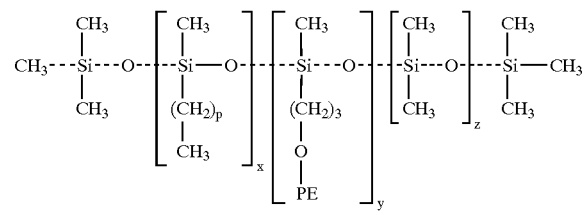

wherein p is 0–40, preferably 12–20, most preferably 15, and

PE is (—C$_2$H$_4$O)$_a$(—C$_3$H$_6$O)$_b$—H where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark. These emulsifiers are represented by the following generic formulas:

(Me$_3$Si)$_{y-2}$[(OSiMe$_2$)$_{x/y}$O—PE]$_y$ wherein PE=—(EO)$_m$(PO)$_n$R
R=lower alkyl or hydrogen
Me=methyl
EO is polyethyleneoxy
PO is polypropyleneoxy
m and n are each independently 1–5000
x and y are each independently 0–5000, and

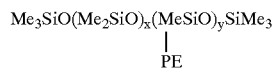

wherein PE=—CH$_2$CH$_2$CH$_2$O(EO)$_m$(PO)$_n$Z
Z=lower alkyl or hydrogen, and
Me, m, n, x, y, EO and PO are as described above, with the proviso that the molecule contains a lipophilic portion and a hydrophilic portion. Again, the lipophilic portion can be supplied by a sufficient number of methyl groups on the polymer Also suitable as nonionic silicone surfactants are hydroxy-substituted silicones such as dimethiconol, which is defined as a dimethyl silicone substituted with terminal hydroxy groups.

Examples of silicone surfactants are those sold by Dow Coming under the tradename Dow Corning 3225C Formulation Aid, Dow Coming 190 Surfactant, Dow Coming 193 Surfactant, Dow Corning Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Shampoo

In addition to containing the ranges of cross-linkable polymer, cross-linking agent, and blocking agent mentioned previously, shampoo compositions in accordance with the invention comprise 0.5–30% of a cleansing surfactant and 10–95% water. Suitable cleansing surfactants include anionic, amphoteric, nonionic, or zwitterionic surfactants.

Anionic surfactants include alkyl and alkyl ether sulfates generally having the formula ROSO$_3$M and RO(C$_2$H$_4$O)$_x$SO$_3$M wherein R is alkyl or alkenyl of from about 10 to 20 carbon atoms, x is 1 to about 10 and M is a water soluble cation such as amnonium, sodium, potassium, or triethanolamine cation.

Another type of anionic surfactant which may be used in the compositions of the invention are water soluble salts of organic, sulfuric acid reaction products of the general formula:

R$_1$—SO$_3$—M wherein R$_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of C$_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

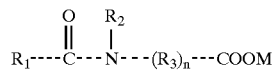

wherein R$_1$ is a C$_{8-24}$ alkyl or alkenyl radical, preferably C$_{10-18}$; R$_2$ is H, C$_{1-4}$ alkyl, phenyl, or —CH$_2$COOM; R$_3$ is CX$_2$— or C$_{1-2}$ alkoxy, wherein each X independently is H or a C$_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Suitable nonionic surfactants are those mentioned above.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

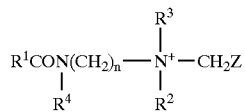

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium. cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants includ aminoalkanoates of the formula

or iminodialkanoates of the formula:

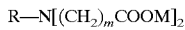

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

Zwitterionic surfactants are also suitable for use in the compositions of the invention. The general formula for such surfactants is:

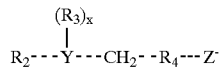

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like.

Shampoo compositions may also contain a variety of other ingredients such as conditioning agents (as mentioned above), chelating agents, preservatives, and so on.

Mascara

Mascara compositions in accordance with the invention generally contain, in addition to the ranges of cross-linkable polymer, cross-linking agent, and blocking agent, 0.1–30% wax, 0.1–50% oil, 0.1–50% particulate matter, and 0.1–10% emulsifier. Suitable waxes, oils, and particulate matter are as mentioned above.

Face Makeup

Face makeup compositions in accordance with the invention generally are water-in-oil or oil-in-water emulsion foundation compositions, or color cosmetics such as makeup, blush, concealer, and the like. Typically, emulsions may comprise 10–95% water and 10–95% oil, in addition to pigments. Anhydrous compositions such as blush, eyeshadow, and the like may comprise 1–95% particulates, 0.5–30% oil, and other ingredients. Suitable particulates, oils and particulates are as mentioned above.

The invention will be further described in connection with the following examples which are set forth for the purpose of illustration only.

EXAMPLE 1

A nail enamel composition in accordance with the invention incorporates a water dispersible, crosslinkable acrylic film-forming polymer which further comprises a volatile, nitrogen-based blocking agent was made as follows:

|  | w/w % |  |
| --- | --- | --- |
| EPS 2538* | 77.4 | film forming polymer + cross-linking agent + dissipatable blocking agent |
| 1-butoxy-2-propanol | 5.1 | solvent |
| Dipropylene glycol monomethyl ether | 5.1 | solvent |
| Water | 12.4 |  |

*experimental self cross-linking acrylic emulsion manufactured by Engineered Polymer Solutions, Inc., Marengo, Illinois.

The composition was made by preparing the water/solvent mixture. This mixture was added to the EPS 2538 with stirring.

EXAMPLE 2

A nail enamel composition in accordance with the invention incorporates a water dispersible, crosslinkable acrylic film-forming polymer which further comprises a volatile, nitrogen-based blocking agent was made according to the following formula:

|  | w/w % |  |
| --- | --- | --- |
| Neocryl XK-12* | 84.7 | (film forming polymer + cross linking agent + blocking agent) |
| Water | 14.9 |  |
| 1-butoxy-2-propanol | 0.2 | (solvent) |
| Dipropylene glycol monomethyl ether | 0.2 | (solvent) |

*NeoCryl XK-12, self-crosslinking acrylic emulsion manufactured by Zeneca Resins, Wilmington, MA.

The composition was made by combining the water and solvents. The film-forming polymer composition was added and the mixture was stirred well.

EXAMPLE 3

A liquid ink composition for use as a semi-permanent skin tattoo in accordance with the invention incorporates a water soluble, crosslinkable poly(vinyl alcohol) film-forming polymer which further comprises a zirconium ammonium carbonate crosslinking agent using water as the solvent-based blocking agent was made as follows:

|  | w/w % |  |
| --- | --- | --- |
| Poly(vinyl alcohol) (10% aqueous solution) | 89.50 | (film-forming polymer + blocking agent) |
| Zirconium ammonium carbonate (20% aqueous solution) | 0.50 | (cross-linking agent) |
| Pigment blend* | 10.00 | |

*20% by weight FD&C Red 6 Ca Lake, 20% by weight water, 60% by weight of a 10% aqueous solution of polyvinyl alcohol.

A 10% solution of poly(vinyl alcohol) in water was prepared. A 20% solution of zirconium ammonium carbonate in water was prepared. Then 99.5% by weight of the PVA solution was combined with 0.5% by weight of the zirconium ammonium carbonate solution and mixed well.

EXAMPLE 4

A solvent-based clear nail enamel was prepared as follows:

|  | w/w % |  |
| --- | --- | --- |
| Acrylic copolymer solution* | 37.80 | (film-forming polymer) |
| Amino silicone** | 2.00 | (cross-linking agent) |
| Butyl acetate | 20.30 | (solvent) |
| Ethyl acetate | 37.20 | (solvent) |
| Pigment | 1.75 | (pigment) |
| Stearalkonium bentonite | 0.95 | (pigment suspending agent) |

*a polymer solution of 70% by weight butyl methacrylate, 20% by weight acetoacetoxymethacrylate, and 10% by weight acrylic acid, having 50% solids.
**An aminofunctional siloxane sold by Wacker Silicones Corporation under the tradename VP 1472M, also known under the tradename CT 250M, which is a textile softener having an amine value of 0.50 and a viscosity of 1000 mm$^2$/s.

The composition was prepared by combining the polymers, solvents, pigment, and other ingredients and mixing well.

EXAMPLE 5

A pigmented water-based nail enamel was prepared as follows:

|  | w/w % |
| --- | --- |
| EPS 2538 | 66.3 |
| Water | 10.7 |
| Dipropylene glycol methyl ether | 4.3 |
| Propylene glycol n-butyl ether | 4.2 |
| D&C Red #6 Ca Lake | 2.0 |
| RBH Red 50992* | 13.5 |

*a dispersion containing 60% by weight red iron oxide, 28.65% by weight deionized water, and 6.35% by weight binder, manufactured by RBH Dispersions, Inc., Bound Brook, New Jersey.

Water and the glycol ethers were combined with mixing. The composition was added slowly to the EPS 2538. Pigments were added and the mixture was sonulated for several minutes.

EXAMPLE 6

A pigmented gel composition for application to lips was prepared as follows:

|  | w/w % |
| --- | --- |
| EPS 2538 | 44.2 |
| Water | 34.6 |
| Propylene glycol n-butyl ether | 2.9 |
| Dipropylene glycol methyl ether | 2.9 |
| Acculyn 44 (Urethane PEG $C_{1-20}$ copolymer) | 0.7 |
| Trioctyldodecyl citrate | 2.5 |
| D&C Red #7 (50% in trioctyldodecyl citrate) | 10.0 |
| PEG-20 stearate | 0.3 |
| Caprylic/capric triglycerides | 0.5 |
| PEG-32 stearate | 0.4 |
| Mica | 1.0 |

Water, glycol ethers, and Acculyn 44 were combined and mixed well. The mixture was slowly added to EPS 2538. In a separate container, the trioctyldodecyl citrate, pigment grind, emulsifiers, and caprylic/capric triglycerides were combined and heated to 85° C. The mixture was allowed to cool to 35° C. The polymer mixture was slowly added to the pigment/emulsifier mixture and mixed well.

EXAMPLE 7

A composition which reduces the perception of facial wrinkling was prepared by mixing a cross-linkable silicone elastomer with a platinum catalyst. Both materials are sold by Dow Coming Corporation under the tradenames MDX4-4210 and X7-4911 respectively. The catalyst promoted a hydrosilylation reaction to cause cross-linking of the silicone elastomer on the face. Blocking was effected by bulking ligands on the metal catalyst which dissociated when the composition was applied to the face to permit cross-linking. The composition was as follows:

|  | grams | w/w % |
| --- | --- | --- |
| MDX4-4210 | 10 | 59 |
| X7-4911 | 7 | 41 |

Ninety nine parts of the above composition was mixed with 1 part of Novacite (a filler). The composition was applied to the skin and formed a translucent film with good "memory" and flexibility. The film provided good concealing of wrinkles.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A composition for treating hair and applying semi-permanent crosslinked film thereon, comprising:
   (a) a film-forming polymer having functional groups capable of cross-linking upon exposure to a cross-linking agent reactive with said functional groups,
   (b) a cross-uniting agent reactive with said functional groups of the film-forming polymer,
   (c) a dissipatable blocking agent which (i) is operable prior to dissipation, to block the cross-linking agent from cross-linking the functional groups of the film-forming polymer, and which, (ii) after dissipation, leaves the cross-linking agent free to cross-link the functional groups of the film-forming polymer.

2. The composition of claim 1 which is for cleansing, conditioning, or coloring hair.

3. The composition of claim 1 which is a shampoo.

4. The composition of claim 3 comprising 0.5–30% of a cleansing surfactant and 10–95% water.

5. The composition of claim 4 wherein the cleansing surfactant is an anionic surfactant.

6. The composition of claim 1 which is a hair conditioner.

7. The composition of claim 6 comprising 0.1–20% of a cationic agent and 5–95% water.

8. The composition of claim 7 further comprising 0.1–30% fatty alcohol and 0.001–10% nonionic surfactant.

9. The composition of claim 1 wherein the functional groups of the film-forming polymer are carboxylic acid, hydroxyl, or combinations thereof.

10. The composition of claim 2 wherein the film-forming polymer is comprised of monomers selected from the group consisting of:

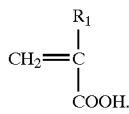  I

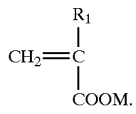  II

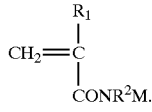  III wherein $R_1$ is H or a $C_{1-30}$ straight or branched chain alkyl, aryl, or aralkyl; $R^2$ is H or $C_{1-30}$ straight or branched chain alkyl, aryl, or aralkyl; and M is a $C_{1-30}$ straight or branched chain alkyl which is unsubstituted, or substituted with one or more substitutents which are hydroxyl, halogen, carboxyl, acetoacetoxy, or combinations thereof; pyrrolidone, or a Substituted or unsubstituted aromatic, alicyclic, or bicyclic ring where the substitutents are $C_{1-30}$ straight or branched chain alkyl.

11. The composition of claim 1 wherein the cross-linking agent is an aliphatic or aromatic dihydric alcohol, an alphatic or aromatic polyol, a metal ion having a coordination number ranging from 2 to 4, amine, or mixtures thereof.

12. The composition of claim 1 wherein the dissipatable blocking agent comprises a cosmetically acceptable carrier phase comprising a solvent.

13. The composition of claim 12 wherein the solvent in the carrier phase comprise water, a non-aqueous volatile solvent, or mixtures thereof.

14. A composition for conditioning hair and applying semi-permanent crosslinked film thereon, comprising:

(a) a film-forming polymer having functional groups capable of cross-linking upon exposure to a cross-linking agent reactive with said functional groups, (b) a cross-linking agent reactive with said functional groups of the film-forming polymer (c) a dissipatable blocking agent which (i) is operable prior to dissipation, to block the cross-linking agent from cross-linking the functional groups of the film-forming polymer, and which, (ii) after dissipation, leaves the cross-linking agent free to cross-link the functional groups of the film-forming polymer, at least one hair conditioning ingredient; and water.

15. The composition of claim 14 wherein the at least one hair conditioning agent comprises one or more cationic quaternary ammonium compounds, fatty alcohols, or mixtures thereof.

16. A composition for cleansing hair and applying semi-permanent crosslinked film thereon, comprising:

(a) film-forming polymer having functional groups capable of cross-linking upon exposure to a cross-linking agent reactive with said functional groups, (b) a cross-linking agent reactive with said functional groups of the film-forming polymer, (c) a dissipatable blocking agent which (i) is operable prior to dissipation, to block the cross-linking agent from cross-linking the functional groups of the film-forming polymer, and which, (ii) after dissipation, leaves the cross-linking agent free to cross-link the functional groups of the film-forming polymer, at least one cleansing surfactant; and water.

17. The composition of claim 16 wherein the cleansing surfactant comprises an anionic surfactant, a nonionic surfactant, an amphoteric surfactant, a zwitterionic surfactant, or mixtures thereof.

* * * * *